United States Patent
Cai et al.

(10) Patent No.: US 6,281,211 B1
(45) Date of Patent: Aug. 28, 2001

(54) SUBSTITUTED SEMICARBAZIDES AND THE USE THEREOF

(75) Inventors: Sui Xiong Cai, San Diego; Nancy C. Lan, South Pasadena; Soo Hong-Bae, Diamond Bar, all of CA (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 09/601,698

(22) PCT Filed: Feb. 4, 1999

(86) PCT No.: PCT/US99/02419

§ 371 Date: Sep. 21, 2000

§ 102(e) Date: Sep. 21, 2000

(87) PCT Pub. No.: WO99/39712

PCT Pub. Date: Aug. 12, 1999

(51) Int. Cl.[7] .................. A61K 31/535; C07D 207/04; C07D 211/70; C07D 251/00; C07D 307/02; C07C 281/00

(52) U.S. Cl. .................. 514/237.5; 514/238.2; 514/241; 514/247; 514/269; 514/311; 514/315; 514/459; 514/590; 544/111; 544/158; 544/162; 544/215; 544/238; 546/175; 546/332; 548/567; 548/569; 549/426; 549/487; 549/491; 564/34; 564/35

(58) Field of Search .................. 514/237.5, 238.2, 514/241, 247, 269, 311, 315, 459, 590; 544/111, 158, 162, 215, 238; 546/175, 332; 548/567, 569; 549/426, 487, 491; 564/34, 35

(56) References Cited

U.S. PATENT DOCUMENTS

| | | | |
|---|---|---|---|
| 3,576,864 | 4/1971 | Kuppuswamy | 514/34 |
| 4,725,608 | 2/1988 | Nakaguchi et al. | 514/353 |
| 5,236,957 | 8/1993 | Dostert et al. | 514/620 |
| 5,446,066 | 8/1995 | Varasi et al. | 514/620 |
| 5,449,692 | 9/1995 | Varasi et al. | 514/620 |
| 5,741,818 | 4/1998 | Dimmock | 514/590 |

FOREIGN PATENT DOCUMENTS

| | | |
|---|---|---|
| WO 90/14334 | 11/1990 | (WO) . |
| WO 96/40628 | 12/1996 | (WO) . |
| WO 97/05102 | 2/1997 | (WO) . |
| WO 98/19998 | 5/1998 | (WO) . |
| WO 98/43964 | 10/1998 | (WO) . |
| WO 98/47869 | 10/1998 | (WO) . |
| WO 99/26614 | 6/1999 | (WO) . |
| WO 99/39712 | 8/1999 | (WO) . |

OTHER PUBLICATIONS

Titles of Scrip Articles Concerning *SCRIP World Pharmaceutical News* 1773 : 14 (1992), and abstract "Neurogen licenses National Institutes of Health (NIH) anticonvulsants," *SCRIP World Pharmaceutical News* 1701 : 21 (1992). PJB Publications Ltd, [retrievable from: Pharmaceutical and Healthcare Industry News Database (PHIND) –weekly [online]].
"Wellcome's 46% profit rise in 1993 fails to impress," *SCRIP World Pharmaceutical News* 1870:8 (1993) and "Cambridge Neuroscience's grant for channel blockers," *SCRIP World Pharmaceutical News* 1820:16 (1993). PJB Publications Ltd, [retrievable from: Pharmaceutical and Healthcare Industry News Database (PHIND) –weekly [online] ].
Bensimon, G., et al., "A Controlled Trial of Riluzole in Amyotrophic Lateral Sclerosis," *New Engl. J. Med.* *330*:585–591, Massachusetts Medical Society (1994).
Brown, C.M., et al., "Neuroprotective properties of lifarizine compared with those of other agents in a mouse model of focal cerebral ischaemia," *British J. Pharmol.* 115:1425–1432, Stockton Press (1995).

(List continued on next page.)

Primary Examiner—John Kight
Assistant Examiner—Raymond Covington
(74) Attorney, Agent, or Firm—Sterne, Kessler, Goldstein & Fox P.L.L.C.

(57) ABSTRACT

This invention is related to substituted semicarbazides represented by Formula (I) or a pharmaceutically acceptable salt or prodrug thereof, wherein: $R_1$ and $R_2$ are independently hydrogen, alkyl, cycloalkyl, alkenyl, alkynyl, haloalkyl, aryl, aminoalkyl, hydroxyalkyl, alkoxyalkyl or carboxyalkyl; $R_3$, $R_4$, $R_5$ and $R_6$ are independently hydrogen, alkyl, cycloalkyl, alkenyl, alkynyl, haloalkyl, aryl, aminoalkyl, hydroxyalkyl, alkoxyalkyl or carboxyalkyl, or $R_3$ and $R_4$ is defined as above, and $R_5$ and $R_6$ together with the nitrogen atom to which they are attached form a heterocycle, including piperidine, piperazine, morpholine; $A_1$ and $A_2$ are independently aryl, heteroaryl, saturated or partially unsaturated carbocycle or saturated or partially unsaturated heterocycle, any of which is optionally substituted; X is one of O, S, $NR_7$, $CH_2$, $C(O)$, $NR_7C(O)$, $C(O)NR_7$, SO, $SO_2$ or a covalent bond; where $R_7$ is hydrogen, alkyl, cycloalkyl, alkenyl, alkynyl, haloalkyl, aryl, aminoalkyl, hydroxyalkyl, alkoxyalkyl or carboxyalkyl; n is 0, 1, 2 or 3. m is 0, 1, 2 or 3. The invention also is directed to the use of substituted semi-carbazides for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as anticonvulsants, and as antimanic depressants, as anti-nigraine agents, as local anesthetics, as antiarrhythmics and for the treatment or prevention of diabetic neuropathy.

(I)

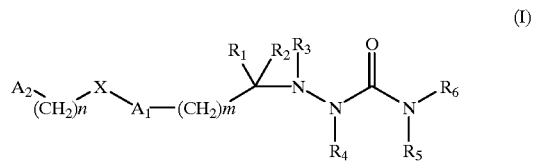

21 Claims, No Drawings

OTHER PUBLICATIONS

Catterall, W. A., "Common modes of drug action on Na⁺ channels: local anesthetics, antiarrhythmics and anticonvulsants," *Trends Pharmacol. Sci.* 8:57–65 Elsevier Science Publishers B.V. (1987).

Catteral, W. A., "Neurotoxins That Act on Voltage–Sensitive Sodium Channels in Excitable Membranes," *Ann. Rev. Pharmacol. Toxicol.* 20:15–43, Annual Reviews, Inc. (1980).

Taylor, C. P. and Meldrum, B.S., "Na⁺ channels as targets for neuroprotective drugs,"*Trends Pharmacol. Sci. 16*:309–316, Elsevier Science Publishers B.V. (1995).

International Search Report for PCT/US99/02419 (May 28, 1999).

Catterall, W. A., "Structure and Function of Voltage–Sensitive Ion Channels, " *Science 242*:50–61, Association for the Advancement of Science (1988).

Denicoff, K. D., et al., "Efficacy of Carbamazepine Compared With Other Agents: A Clinical Practice Survey,"*J. Clin. Psychiatry 55*:70–76, Physicians Postgraduate Press Inc. (1994).

Dimmock, J. R., et al., "(Aryloxy) aryl Semicarbazones and Related Compounds: A Novel Class of Anticonvulsant Agents Possessing High Activity in the Maximal Electroshock Screen," *J. Med. Chem.* 39:3984–3997, American Chemical Society (1996).

Graham, S. H., et al., "Neuroprotective Effects of a Use–Dependent Blocker of voltage–Dependent Sodium Channels, BW619C89, in Rat Middle Cerebral Artery Occlusion,"*J. Pharmacol. Exp. Ther.* 269:854–859, The American Society for Pharmacology and Experimental Therapeutics (1994).

Pevarello, P., et al., "Synthesis and Anticonvulsant Activity of a New Class of 2–[(Arylalkyl)amino]alkanamide Derivatives,"*J. Med. Chem.* 41:579–590, American Chemical Society (1998).

Stys, P. K., et al., "Ionic Mechanism of Anoxic Injury in Mammalian CNS White Matter: Role of Na⁺ Channels and Na⁺–Ca²⁺ Exchanger," *J. Neurosci.* 12:430–439, Society for Neuroscience (1992).

SUBSTITUTED SEMICARBAZIDES AND THE USE THEREOF

This application is A 371 of PCT/US 99/02419 filed Feb. 4, 1999.

BACKGROUND OF THE INVENTION

1. Field of the Invention

This invention is in the field of medicinal chemistry. In particular, the invention relates to novel substituted semicarbazides and the discovery that these compounds are anticonvulsants and act as blockers of sodium ($Na^+$) channels.

2. Related Background Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine. have been shown to share a common mechanism of action by blocking or modulating $Na^+$ channel activity (Catterall, W. A., *Trends Pharmacol. Sci.* 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., *J. Pharmacol. Exp. Ther.* 269:854–859 (1994); Brown et al., *British J. Pharmacol.* 115:1425–1432 (1995); *SCRIP* 1870:8 (1993); *SCRIP* 1773:14 (1992)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., *J. Neurosci.* 12:430–439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., *New Engl. J. Med.* 330:585–591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, *Trends Pharmacol. Sci.* 16:309–316 (1995)), and carbamazepine and lamotrigine have been used for the treatment of manic depression (Denicott et al., *J. Clin. Psychiatry* 55: 70–76 (1994)).

It has been established that there are at least five to six sites on the voltage-sensitive $Na^+$ channels which bind neurotoxins specifically (Catterall, W. A., *Science* 242:50–61 (1988)). Studies have further revealed that therapeutic antiarrhythmics, anticonvuisants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., *Ann. Rev. Pharmacol. Toxicol.* 10:15–43 (1980)).

PCT International Published Application WO96/40628 discloses semicarbazones represented by the following Formula:

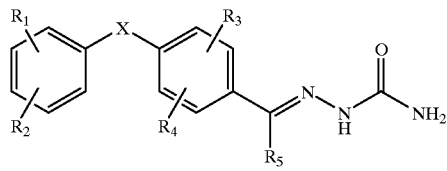

where $R_1$–$R_4$ are independently hydrogen, halogen, $C_{1-9}$ alkyl, $C_{3-9}$ cycloalkyl, cyano, $C_{1-9}$ alkoxy, or $C_{6-10}$ aryloxy; $R_5$ is hydrogen, $C_{1-9}$ alkyl, $C_{3-9}$ cycloalkyl, or $C_{6-10}$ aryl; and X is oxygen or sulfur. The compounds are disclosed to be useful as anticonvulsants. However, it was not suggested or implicated that semicarbazides, which can be prepared by reduction of the semicarbazones, also will act as anticonvulsants.

Dimmock et al., *J. Med. Chem.* 39:3984–3997 (1996) discloses (aryloxy)aryl semicarbazones that displayed anticonvulsant activities when administered intraperitoneally to mice or orally to rats. However, it was not suggested or implicated that semicarbazides, which can be prepared by reduction of the semicarbazones, also will act as anticonvulsants.

SUMMARY OF THE INVENTION

The present invention is related to the surprising discovery that novel substituted semicarbazides represented by Formula I are anticonvulsants and act as blockers of sodium ($Na^+$) channels. Although the semicarbazides of Formula I can be prepared by reduction of the corresponding semicarbazones, semicarbazides and semicarbazones are two different classes of compounds. Semicarbazide is a base due to the presence of the basic N-1 nitrogen. Semicarbazone is not a base but the NH group on N-2 nitrogen is slightly acidic. The C=N double bond in semicarbazone make it a relatively rigid molecule. The C—N single bond in semicarbazide make it a relatively non-rigid molecule. Therefore it is a surprising discovery that semicarbazides of this invention as represented by Formula I are anticonvulsants and act as blockers of sodium ($Na^+$) channels, similar to semicarbazones. The invention is also related with treating a disorder responsive to the blockade of sodium channels in a mammal suffering from excess activity of said channels by administering an effective amount of a compound of Formula I as described herein.

The present invention is also directed to the use of a compound of Formula I for the treatment of neuronal damage following global and focal ischemia, and for the treatment or prevention of neurodegenerative conditions such as amyotrophic lateral sclerosis (ALS), as antimanic depressants, as local anesthetics, as antiarrhythmics, as anticonvulsants and for the treatment or prevention of diabetic neuropathy and for the treatment of pain including both acute and chronic pain and migraine headache.

A first aspect of the present invention is directed to the novel substituted semicarbazides of Formula I.

A second aspect of the present invention is directed to the novel compounds of Formula I as blockers of sodium channels.

A third aspect of the present invention is to provide a method for treating, preventing or ameliorating neuronal loss following global and focal ischemia; treating, preventing or ameliorating pain including acute and chronic pain, and neuropathic pain; treating, preventing or ameliorating neurodegenerative conditions; treating, preventing or ameliorating manic depression; treating local anesthesia, arrhythmias, and convulsion by administering a compound of Formula I to a mammal in need of such treatment.

A fourth aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

A fifth aspect of the present invention is directed to methods for preparing novel compounds of Formula I.

DETAILED DESCRIPTION OF THE INVENTION

The present invention arises out of the discovery that novel substituted semicarbazides of Formula I are anticonvulsants and act as blocker of the $Na^+$ channel. In view of this discovery, compounds of Formula I are useful for treating disorders responsive to the blockade of sodium ion channels.

The compounds useful in this aspect of the present invention are novel substituted semicarbazides represented by Formula I:

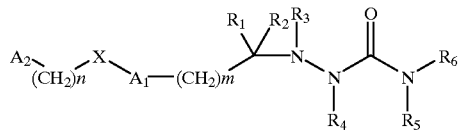

or a pharmaceutically acceptable salt or prodrug thereof, wherein:

$R_1$ and $R_2$ are independently hydrogen, alkyl, cycloalkyl, alkenyl, alkynyl, haloalkyl, aryl, aminoalkyl, hydroxyalkyl, alkoxyalkyl or carboxyalkyl;

$R_3$, $R_4$, $R_5$ and $R_6$ are independently hydrogen, alkyl, cycloalkyl, alkenyl, alkynyl, haloalkyl, aryl, aminoalkyl, hydroxyalkyl, alkoxyalkyl or carboxyalkyl, or $R_3$ and $R_4$ is defined as above, and $R_5$ and $R_6$ together with the nitrogen atom to which they are attached form a heterocycle, including piperidine, piperazine, morpholine;

$A_1$ and $A_2$ are independently aryl, heteroaryl, saturated or partially unsaturated carbocycle or saturated or partially unsaturated heterocycle, any of which is optionally substituted;

X is one of O, S, $NR_7$, $CH_2$, C(O), $NR_7C(O)$, $C(O)NR_7$, SO, $SO_2$ or a covalent bond; where $R_7$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3, m is 0, 1, 2, or 3.

Preferred compounds falling within the scope of Formula I include compounds wherein $A_1$ and $A_2$ are both aryl moieties, preferably both phenyl moieties, that are each optionally independently substituted by one to four substituents independently selected from the group consisting of halogen, nitro, amino, $C_{1-6}$ alkyl, $C_{1-6}$ haloalkyl, $C_{3-8}$ cycloalkyl, cyano, $C_{1-6}$ alkoxy or $C_{6-10}$ aryloxy; $R_1$ and $R_2$ is independently hydrogen, $C_{1-6}$ alkyl, $C_{3-8}$ cycloalkyl or $C_{6-10}$ aryl; $R_3$, $R_4$, $R_5$ and $R_6$ are independently hydrogen or $C_{1-6}$ alkyl; X is O; and n and m are 0.

Preferred compounds within Formula I also include those compounds where $A_1$ is an optionally substituted aryl group selected from the group consisting of phenyl and naphthyl, and $A_2$ is an optionally substituted heteroaryl or aryl group selected from the group consisting of pyridyl, pyrimidinyl, 1,3,5-triazinyl, furanyl, thiophenyl, naphthyl, quinolyl, 3,4-methylenedioxyphenyl, 3,4-ethylenedioxyphenyl, indanyl, tetrahydronaphthyl and quinoxalinyl. Also including are biphenylmethyl and triphenylmethyl.

Additional preferred compounds within Formula I also include those compounds where $A_1$ is an optionally substituted aryl group selected from the group consisting of phenyl or naphthyl, and $A_2$ is an optionally substituted carbocycle or heterocycle selected from the group consisting of cyclopentyl, cyclohexyl, cycloheptyl, piperidinyl, morpholinyl, pyrrolidinyl, tetrahydrofuranyl, tetrahydropyranyl, cyclohexenyl, adamantyl, exo-norbornyl and cyclopentenyl.

Additional preferred compounds within Formula I include those compounds where $A_1$ is an optionally substituted heteroaryl or aryl group selected from the group consisting of pyridyl, pyrimidinyl, 1,3,5-triazinyl, naphthyl, quinolyl, furanyl, and thiophenyl, and $A_1$ is an optionally substituted heteroaryl or aryl group selected from the group consisting of phenyl, furanyl, thiophenyl, quinolinyl, 3,4-methylenedioxyphenyl, 3,4-ethylenedioxyphenyl, indanyl, tetrahydronaphthyl and naphthyl.

Additional preferred compounds within Formula I include those compounds where $A_1$ is an optionally substituted, saturated or partially unsaturated carbocycle or heterocycle selected from the group consisting of cyclopentyl, cyclohexyl, cycloheptyl, morpholinyl, piperidinyl, pyrrolidinyl, tetrahydrofuranyl and tetrahydropyranyl, and $A_2$ is an optionally substituted aryl or heteroaryl group selected from the group consisting of phenyl, furanyl, thiophenyl, quinolinyl, 3,4-methylenedioxyphenyl, 3,4-ethylenedioxyphenyl, indanyl, tetrahydronaphthyl, or naphthyl.

Exemplary preferred compounds that may be employed in this method of invention include, without limitation:

1-(4-phenoxybenzyl)semicarbazide;

1-(4-(4-fluorophenoxy)benzyl)semicarbazide;

1-(4-(4-chlorophenoxy)benzyl)semicarbazide;

1-(4-(4-bromophenoxy)benzyl)semicarbazide;

1-(4-(4-methoxyphenoxy)benzyl)semicarbazide;

1-(4-(4-trifluoromethylphenoxy)benzyl)semicarbazide;

1-(4-(4-methylphenoxy)benzyl)semicarbazide;

1-(4-(3,4-difluorophenoxy)benzyl)semicarbazide;

1-(4-(4-chloro-2-fluorophenoxy)benzyl)semicarbazide;

1-(4-(4-nitrophenoxy)benzyl)semicarbazide;

1-(4-(3-methylphenoxy)benzyl)semicarbazide;

1-(4-(4-t-butylphenoxy)benzyl)semicarbazide;

1-(4-(4-propylphenoxy)benzyl)semicarbazide;

1-(4-(4-s-butylphenoxy)benzyl)semicarbazide;

1-(4-(3,4-methylenedioxyphenoxy)benzyl) semicarbazide;

1-(4-cyclohexyloxybenzyl)semicarbazide;

1-(4-cycloheptyloxybenzyl)semicarbazide;

1-(4-(5-indanyloxy)benzyl)semicarbazide;

1-(4-(6-quinolinyloxy)benzyl)semicarbazide;

1-(4-(4-fluorophenoxy)-3-fluorobenzyl)semicarbazide;

1-(4-(tetrahydropyranyloxy)benzyl)semicarbazide;
1-(4-(4-fluorophenoxy)benzyl-4-methylsemicarbazide; and
1-(4-(4-fluorophenoxy)benzyl)-2-methylsemicarbazide.

Since the compounds of Formula I are blockers of sodium ($Na^+$) channels, a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma; as well as treating or ameliorating neurodegenerative diseases including Alzheimer's disease, amyotrophic lateral sclerosis, Parkinson's disease, treating or ameliorating anxiety, convulsions, glaucoma, migraine headache, and muscle spasm. The compounds of Formula I are also useful as antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

Specifically, preferred substituted semicarbazides are represented by Formulae II-VI. In particular, a preferred embodiment is represented by Formulae II:

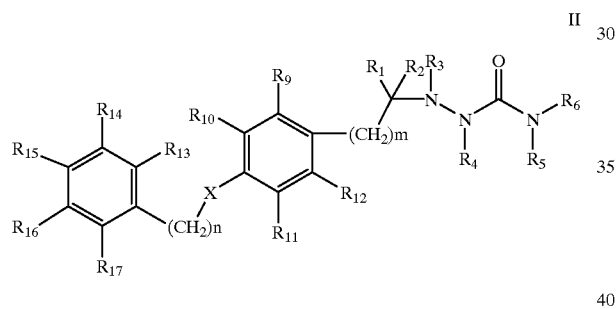

II or a pharmaceutically acceptable salt or prodrug thereof, wherein:

$R_1$, $R_2$, $R_3$, $R_4$, $R_5$, $R_6$, X, n and m are as defined previously with respect to Formula I; and $R_9$, $R_{10}$, $R_{11}$ and $R_{12}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, hetroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamido, hydroxy, thiol, acyloxy, azido, alkoxy, carboxy, carbonylamido or alkylthiol; or $R_9$ and $R_{10}$ or $R_{11}$ and $R_{12}$ are taken together with the carbon atoms to which they are attached to form a carbocycle or heterocycle. Examples of bridges formed by $R_9$ and $R_{10}$ or $R_{11}$ and $R_{12}$ taken together are —$OCH_2O$—, —$OCF_2O$—, —$(CH_2)_3$—, —$(CH_2)_4$—, —$OCH_2CH_2O$—, —$CH_2N(R_{18})CH_2$—, —$CH_2CH_2N(R_{18})CH_2$—, —$CH_2N(R_{18})CH_2CH_2$— and —CH=CH—CH=CH—; where $R_{18}$ is hydrogen, alkyl or cycloalkyl;

$R_{13}$, $R_{14}$, $R_{15}$, $R_{16}$ and $R_{17}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, hetroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamido, hydroxy, thiol, acyloxy, azido, alkoxy, carboxy, carbonylamido or alkylthiol; or one of $R_{13}$ and $R_{14}$ or $R_{14}$ and $R_{15}$, or $R_{15}$ and $R_{16}$, or $R_{16}$ and $R_{17}$ are taken together with the carbon atoms to which they are attached to form a carbocycle or heterocycle. Examples of bridges formed by $R_{13}$ and $R_{14}$, or $R_{14}$ and $R_{15}$, or $R_{15}$ and $R_{16}$, or $R_{16}$ and $R_{17}$ taken together are —$OCH_2O$—, —$OCF_2O$—, —$(CH_2)_3$—, —$(CH_2)_4$—, —$OCH_2CH_2O$—, —$CH_2N(R_{18})CH_2$—, —$CH_2CH_2N(R_{18})CH_2$—, —$CH_2N(R_{18})CH_2CH_2$— and —CH=CH—CH=CH—; where $R_{18}$ is hydrogen, alkyl or cycloalkyl.

Another preferred embodiment of the invention includes substituted semicarbazides represented by Formula III and Formula IV:

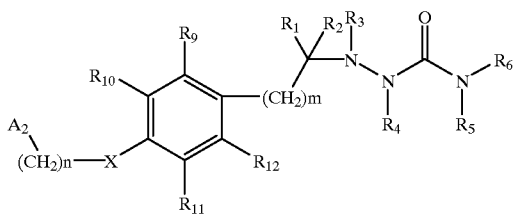

III

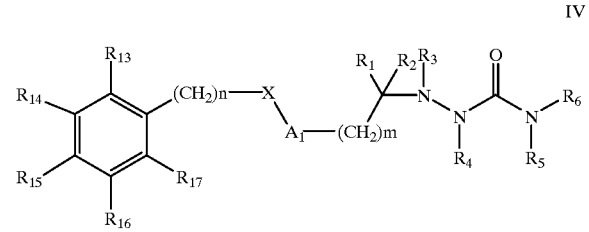

IV or a pharmaceutically acceptable salt or prodrug thereof, wherein:

$R_1$–$R_6$, $R_9$–$R_{12}$, $R_{13}$–$R_{17}$, n, m, $A_1$, $A_2$ and X are as defined previously with respect to Formulae I and II;

Preferred compounds within Formula III include those compounds where $A_2$ is an optionally substituted heteroaryl or aryl group selected from the group consisting of pyridyl, pyrimidinyl, 1,3,5-triazinyl, naphthyl, quinolyl, furanyl, and thiophenyl.

Preferred compounds within Formula IV include those compounds where $A_1$ is an optionally substituted heteroaryl or aryl group selected from the group consisting of pyridyl, pyrimidinyl, 1,3,5-triazinyl, naphthyl, quinolyl, furanyl, and thiophenyl.

Another preferred embodiment of the invention includes substituted semicarbazides represented by Formula V and Formula VI:

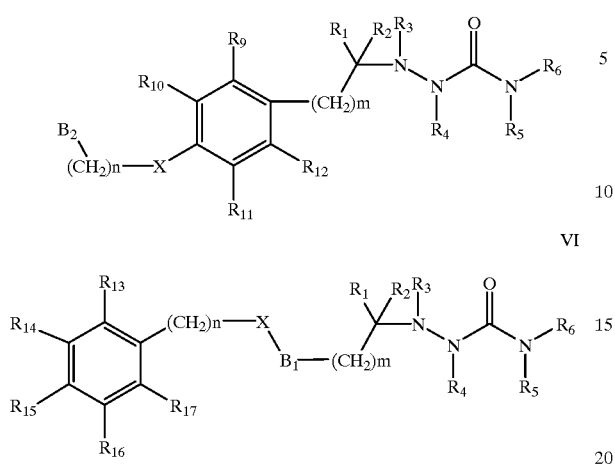

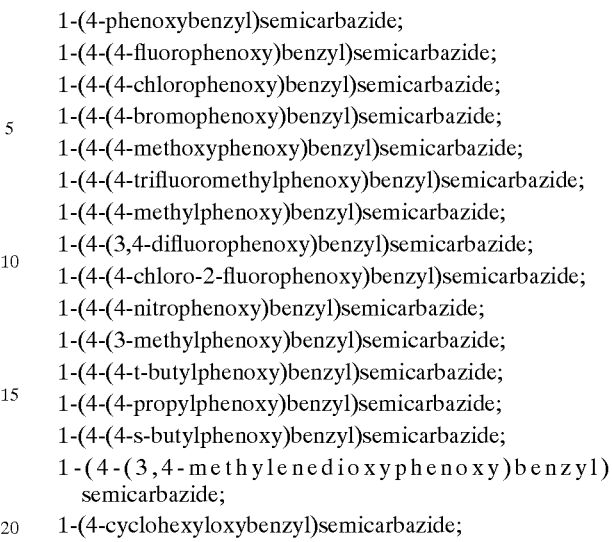

or a pharmaceutically acceptable salt or prodrug thereof, wherein:

$R_1$–$R_6$, $R_9$–$R_{12}$, $R_{13}$–$R_{17}$, n, m and X are as defined previously with respect to Formulae I and II; and $B_1$ is an optionally substituted, saturated or partially unsaturated carbocycle or optionally substituted, saturated or partially unsaturated heterocycle; and $B_2$ is an optionally substituted, saturated or partially unsaturated carbocycle or optionally substituted, saturated or partially unsaturated heterocycle.

Preferred $B_1$ and $B_2$ independently include cyclopentyl, cyclohexyl, cycloheptyl, tetrahydrofuranyl, tetrahydropyranyl, pyrrolidinyl or piperidinyl.

Generally, preferred compounds of Formulae I-VI are those compounds where $R_1$ and $R_2$ is hydrogen or alkyl, more preferably hydrogen, methyl or ethyl, and where $R_3$ and $R_4$ are independently hydrogen or $C_{1-4}$ alkyl.

Preferred values of X in Formulae I-VI are O.

Preferred values of $R_5$–$R_6$ with respect to Formulae I-VI are hydrogen or $C_{1-4}$ alkyl.

Preferred values of $R_9$–$R_{12}$, and $R_{13}$–$R_{17}$, with respect to Formulae II-VI include hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl ($C_2$–$C_6$)alkenyl, $C_{6-C10}$ aryl($C_2$–$C_6$)alkynyl, $C_1$–$C_6$ hydroxyalkyl, nitro, amino, ureido, cyano, $C_1$–$C_6$ acylamido, hydroxy, thiol, $C_1$–$C_6$ acyloxy, azido, $C_1$–$C_6$ alkoxy, or carboxy. Alternatively, $R_9$ and $R_{10}$ or $R_{11}$ and $R_{12}$, or two adjacent $R_{13}$ through $R_{17}$ can form a bridge selected from the group consisting of —OCH$_2$O—, —CH$_2$)$_3$—, —CH$_2$)$_4$—, —OCH$_2$CH$_2$O—, —CH$_2$N(R$_{18}$)CH$_2$—, —CH$_2$CH$_2$N(R$_{18}$)CH$_2$—, —CH$_2$N(R$_{18}$)CH$_2$CH$_2$—, and —CH=CH—CH=CH—, where R18 is hydrogen or $C_1$–$C_6$ alkyl.

With respect to the novel methods of treatment of the present invention, an additional preferred subset of substituted semicarbazides includes compounds of Formula I, wherein $A_1$ and $A_2$ are phenyl moieties, that are each independently substituted by one or two substituents independently selected from the group consisting of hydrogen, halogen, $C_{1-6}$ alkyl, $C_{3-8}$ cycloalkyl, cyano, $C_{1-6}$ alkoxy or $C_{6-10}$ aryloxy; $R_1$ and $R_2$ is hydrogen, $C_{1-6}$ alkyl, or $C_{3-8}$ cycloalkyl; $R_3$ and $R_4$ is hydrogen, or $C_{1-6}$ alkyl; X is O; n and m is 0.

Useful compounds in this aspect of the present invention include:

1-(4-phenoxybenzyl)semicarbazide;
1-(4-(4-fluorophenoxy)benzyl)semicarbazide;
1-(4-(4-chlorophenoxy)benzyl)semicarbazide;
1-(4-(4-bromophenoxy)benzyl)semicarbazide;
1-(4-(4-methoxyphenoxy)benzyl)semicarbazide;
1-(4-(4-trifluoromethylphenoxy)benzyl)semicarbazide;
1-(4-(4-methylphenoxy)benzyl)semicarbazide;
1-(4-(3,4-difluorophenoxy)benzyl)semicarbazide;
1-(4-(4-chloro-2-fluorophenoxy)benzyl)semicarbazide;
1-(4-(4-nitrophenoxy)benzyl)semicarbazide;
1-(4-(3-methylphenoxy)benzyl)semicarbazide;
1-(4-(4-t-butylphenoxy)benzyl)semicarbazide;
1-(4-(4-propylphenoxy)benzyl)semicarbazide;
1-(4-(4-s-butylphenoxy)benzyl)semicarbazide;
1-(4-(3,4-methylenedioxyphenoxy)benzyl) semicarbazide;
1-(4-cyclohexyloxybenzyl)semicarbazide;
1-(4-cycloheptyloxybenzyl)semicarbazide;
1-(4-(5-indanyloxy)benzyl)semicarbazide;
1(4-(6-quinolinyloxy)benzyl)semicarbazide;
1-(4-(4-fluorophenoxy)-3-fluorobenzyl)semicarbazide;
1-(4-(tetrahydropyranyloxy)benzyl)semicarbazide;
1-(4-(4-fluorophenoxy)benzyl-4-methylsemicarbazide; and
1-(4-(4-fluorophenoxy)benzyl)-2-methylsemicarbazide.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl and cyclohexyl and cycloheptyl.

Usefull saturated or partially saturated carbocyclic groups are cycloalkyl groups as defined above, cycloalkenyl groups, such as cyclopentenyl, cycloheptenyl and cyclooctenyl, bicycloalkyl groups such as norbornyl groups, as well as tetrahydronaphthyl and indanyl groups.

Useful halo or halogen groups include fluorine. chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are $C_{2-6}$ alkenyl groups, preferably $C_{2-4}$ alkenyl. Typical $_{2-14}$ alkenyl groups include ethenyl, propenyl, isopropenyl, butenyl, and sec.-butenyl.

Useful alkynyl groups are $C_{2-6}$ alkynyl groups, preferably $C_{2-4}$ alkynyl. Typical $C_{2-14}$ alkynyl groups include ethynyl, propynyl, butynyl, and 2-butynyl groups.

Useful arylalkyl groups include any of the above-mentioned $C_{1-10}$ alkyl groups substituted by any of the above-mentioned $C_{6-14}$ aryl groups. Usefull values include benzyl, phenethyl and naphthylmethyl.

Useful arylalkenyl groups include any of the above-mentioned $C_{2-4}$ alkenyl groups substituted by any of the above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Useful values include phenylethynyl and phenylpropynyl.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl and pyrazolinyl groups.

Useful heterocycloalkyl groups include any of the above-mentioned $C_{1-10}$ alkyl groups substituted by any of the above-mentioned heterocyclic groups.

Useful heteroaryl groups include any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbazolyl, carbazolyl, β-carbolinyl, phenanthridinyl, acrindinyl, perimidinyl, phenanthrolinyl, phenazinyl, isothiazolyl, phenothiazinyl, isoxazolyl, furazanyl. phenoxazinyl, 1,4-dihydroquinoxaline-2,3-dione, 7-aminoisocoumarin pyrido[1,2-a]pyrimidin-4-one, 1,2-benzoisoxazol-3-yl, 4-nitrobenzofurazan, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Useful heteroarylalkyl groups include any of the above-mentioned $C_{1-10}$ alkyl groups substituted by any of the above-mentioned heteroaryl groups.

Useful heteroarylalkenyl groups include any of the above-mentioned $C_{2-4}$ alkenyl groups substituted by any of the above-mentioned heteroaryl groups.

Useful heteroarylalkynyl groups include any of the above-mentioned $C_{2-4}$ alkynyl groups substituted by any of the above-mentioned heteroaryl groups.

Usefull amino groups include —$NH_2$, —$NHR_{14}$, and —$NR_{14}R_{15}$, wherein $R_{14}$ and $R_{15}$ are $C_{1-10}$ alkyl or cycloalkyl groups as defined above.

Useful aminocarbonyl groups are carbonyl groups substituted by —$NH_2$, —$NHR_{14}$, and —$NR_{14}R_{15}$, wherein $R_{14}$ and $R_{15}$ are $C_{1-10}$ alkyl groups.

Optional substituents on any of the aryl, heterocyclic, heteroaryl, and cycloalkyl rings in Formulae I-VI include any one of halo, haloalkyl, aryl, heterocycle, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, hydroxy, thiol, acyloxy, azido, alkoxy, carboxy, aminocarbonyl, and alkylthiol groups mentioned above. Preferred optional substituents include: halo, haloalkyl, hydroxyalkyl, aminoalkyl, nitro. alkyl alkoxy and amino.

Certain of the compounds of Formula I may exist as optical isomers and the invention includes both the racemic mixtures of such optical isomers as well as the individual entantiomers that may be separated according to methods that are well know to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate, acetic acid, dichloroacetic acid and oxalate.

Examples of prodrugs include esters or amides of Formula I with $R_1$–$R_6$ as hydroxyalkyl or aminoalkyl, and these may be prepared by reacting such compounds with anhydrides such as succinic anhydride.

The invention is also directed to a method for treating disorders responsive to the blockade of sodium channels in animals suffering thereof. Particular preferred embodiments of the substituted semicarbazides for use in method of this invention are represented by previously defined Formula I.

The compounds of this invention may be prepared using methods known to those skilled in the art, or by the novel methods of this invention. Compounds with Formulae I-VI can be prepared as illustrated by exemplary reaction in Scheme I from reduction of the corresponding semicarbazones.

Scheme 1

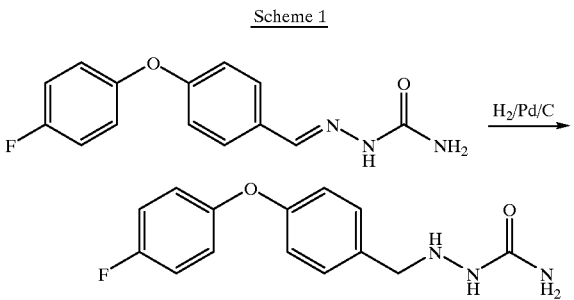

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of $Na^+$ permeability in response to depolarization associated with the action potential in many excitable cells including muscle, nerve and cardiac cells.

One aspect of the present invention is the discovery of the mechanism of action of the compounds herein described as specific $Na^+$ channel blockers. Based upon the discovery of this mechanism, these compounds are contemplated to be useful in treating or preventing neuronal loss due to focal or global ischemia, and in treating or preventing neurodegenerative disorders including ALS, anxiety, and epilepsy. They are also expected to be effective in treating, preventing or ameliorating neuropathic pain, surgical pain and chronic pain. The compounds are also expected to be useful as antiarrhythmics, anesthetics and antimanic depressants.

The present invention is directed to compounds of Formulae I that are blockers of voltage-sensitive sodium channels. According to the present invention, those compounds having preferred sodium channel blocking properties exhibit an $IC_{50}$ of about 100 μM or less in the electrophysiological assay described herein. Preferably, the compounds of the present invention exhibit an $IC_{50}$ of 10 μM or less. Most preferably, the compounds of the present invention exhibit an $IC_{50}$ of about 1.0 μM or less. Substituted semicarbazides of the present invention may be tested for their $Na^+$ channel blocking activity by the following electrophysiological and binding assays.

Electrophysiological Assay:

Cellpreparation: HEK-293 cells stably expressing the hSkM1 isoform of $Na^+$ channels (generous gift from Dr. A. L. George, Vanderbilt University Medical School) were cultured using standard techniques, as described previously (Verdoorn, T. A, et al., *Neuron* 4:919–928 (1990)). For electrophysiology, cells were plated onto 35 mm Petri dishes (pre-coated with poly-D-lysine) at a density of 1:40 on the day of re-seeding from confluent cultures. Cells are suitable for recordings for 2–3 days after plating.

Patch-clamp recordings of voltage-sensitive $Na^+$ currents: Whole-cell voltage-clamp recordings were made using conventional patch-clamp techniques (Hamill et al, *Pfluegers Arch.* 391:85–100 (1981)) with an Axopatch 200 A amplifier (Axon Instruments, Foster City, Calif.). Recordings were made within 2–3 hours after neuron dissociation. The recording chamber was continuously superfused with the external solution (150 mM NaCl, 5.4 mM KCl, 1.8 mM $CaCl_2$, 1 mM $MgCl_2$, 10 mM HEPES, 10 mM glucose, pH 7.4 (NaOH)) at a speed of about 1 ml/min. Recording pipettes were pulled from thick-walled capillaries (WPI, Sarasota, Fla.) and fire-polished. The pipette resistances ranged from 1 to 3 MΩ when the pipettes were filled with internal solution containing (in mM): 110 CsF, 10 NaCl, 5 $MgCl_2$, 11 EGTA, 10 HEPES, pH adjusted to 7.4 with CsOH. Osmolality was set with a difference of 15–20 mmol/kg between external and internal solutions (lower inside the cell). Drugs and intervening wash-outs were applied through a linear array of flow pipes (Drummond Microcaps, 2-μl, 64-mm length). Compounds are dissolved in dimethylsulfoxide (DMSO) to make a 30 mM stock solution, which was subsequently diluted into the external solution to give final concentrations of 0.1–100 μM. At the highest (1%) concentration, DMSO inhibited the size of $Na^+$ current only slightly. Currents were recorded at room temperature (22–25° C.), filtered at 5 kHz with an active 8-pole Bessel filter (Frequency Devices, Haverhill, Mass.), digitized at 10–50-μs intervals, and stored using Digidata 1200 analog/digital interface with Pclamp6/Clampex software (Axon Instruments). Series resistance was cancelled typically by ~75% when necessary. The inhibitory potency of drugs was assessed by measuring reductions in the peak amplitude of $Na^+$ currents induced by increasing concentrations of compounds tested. $Na^+$ currents were elicited by stepping membrane voltage from holding potentials over the range −100 mV to −50 mV, to a pulse potential of −10 mV. The test pulse duration was 5–10 msec, repeated at a frequency ≦1 Hz. Concentration-inhibition curves were fitted with equation 1:

$$I/I_{control} = 1/(1 + ([compound]/IC_{50})) \qquad \text{Eq. 1}$$

where $I_{control}$ is the maximal $Na^+$ current in the absence of antagonist, [compound] is the drug concentration, and $IC_{50}$ is the concentration of compound that produces half maximal inhibition.

Binding Assay:

The ability of compounds of the present invention to modulate either site 1 or site 2 of the $Na^+$ channel was determined following the procedures fully described in Yasushi, *J. Biol. Chem.* 261:6149–6152 (1986) and Creveling, *Mol. Pharmacol.* 23:350–358 (1983), respectively. Rat forebrain membranes were used as sources of $Na^+$ channel proteins. The binding assays were conducted in 130 μM choline chloride at 37° C. for 60-minute incubation with [$^3$H] saxitoxin and [$^3$H] batrachotoxin as radioligands for site 1 and site 2, respectively.

The compounds of the present invention may be tested for in vivo anticonvulsant activity after iv. po or ip injection using a number of anticonvulsant tests in mice (audiogenic seizure model in DBA-2 mice, pentylenetetrazol-induced seizures in mice, maximum electroshock seizure test (MES)).

The compounds may be tested for their neuroprotective activity after focal and global ischemia produced in rats or gerbils according to the procedures described in Buchan et al. (Stroke, Suppl. 148–152 (1993)) and Sheardown et al. (*Eur. J. Pharmacol.* 236:347–353 (1993)) and Graham et al. (*J. Pharmacol Exp. Therap.* 276:1–4 (1996)).

The compounds may be tested for their neuroprotective activity after traumatic spinal cord injury according to the procedures described in Wrathall et. al. (*Exp. Neurology* 137:119–126 (1996)) and Iwasaki et. al. (*J. Neuro Sci.* 134:21–25 (1995)).

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically. the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular 2-aminoacetamide of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the particular 2-aminoacetamide of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates. for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

1-[4-(4-Fluorophenoxy)benzyl]semicarbazide

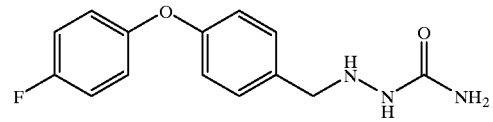

A mixture of 4-(4-fluorophenoxy)benzaldehyde semicarbazone (100 mg, 0.37 mmol) and 5% Pd/C (45 mg) in 15 mL of MeOH was hydrogenated at 1 atm of hydrogen overnight. The catalyst was removed by vacuum filtration over celite and the filtrate was concentrated under reduced pressure to yield a crude product which was purified by flash chromatography using 19:1 ethylacetate/MeOH with few drops of TEA per 100 mL of the solvent mixture to yield 30 mg (38%) of the title compound as a white powder: $^1$H NMR (DMSO-$d_6$) 3.74 (S, 2H), 4.97 (bs, 1H), 5.79 (bs, 2H), 6.91 (d, 2H), 7.00–7.04 (m, 3H), 7.17–7.23 (m, 2H), 7.34 (d, 2H).

EXAMPLE 2

1-[4-(4-Fluorophenoxy)benzyl]-2-methylsemicarbazide

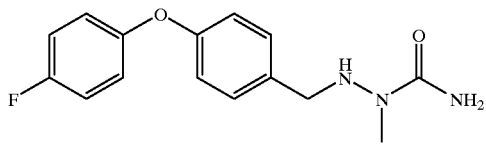

A mixture of 4-(4-fluorophenoxy)benzaldehyde-2'-methyl semicarbazone (103 mg, 0.36 mmol) and 5% Pd/C (45 mg) in 15 mL of MeOH was hydrogenated at 1 atm of hydrogen overnight. The catalyst was removed by vacuum filtration over Celite and the filtrate was concentrated under reduced pressure to yield 101 mg (97%) of the title compound as a white solid: $^1$H NMR (DMSO-$d_6$) 2.91 (s, 3H), 3.79 (d, 2H), 4.50 (t, 1H), 5.94 (bs, 2H), 6.90 (d, 2H), 6.99–7.04 (m, 2H), 7.20 (t, 2H), 7.37 (d, 2H).

The following semicarbazides were prepared from the corresponding semicarbazones using a similar procedure:

1-[4-(cycloheptyloxy)benzyl]semicarbazide;
1-[4-(cyclohexylmethoxy)benzyl]semicarbazide;
1-[3-fluoro-4-(4-fluorophenoxy)benzyl]semicarbazide;
1-[4-(5-indanoxy)benzyl]semicarbazide;
1-[4-(3,4-methylenedioxyphenoxy)benzyl]semicarbazide;
1-[3-(3-methylphenoxy)benzyl]semicarbazide;
1-[4-(trifluoromethyl)benzyl]-2-methylsemicarbazide;
1-[3-fluoro-4-(4-fluorophenoxy)benzyl]-2-methylsemicarbazide;
1-[4-(5,6,7,8-tetrahydro-2-naphthoxy)benzyl]semicarbazide;
1-[3-fluoro-4-(4-Fluorophenoxy)-1-phenylethyl]semicarbazide;
1-[4-(3,4-difluorophenoxy)benzyl]-2-methylsemicarbazide;
1-[4-(3,5-difluorophenoxy)benzyl]semicarbazide;
1-[4-(benzyl)benzyl]semicarbazide;
1-[4-(3,4-methylenedioxyphenoxy)benzyl]-2-methylsemicarbazide;
1-[4-(5,6,7,8-Tetrahydro-2-naphthoxy)benzyl]-2-methylsemicarbazide;
1-[3-fluoro-4-(5-Indanoxy)benzyl]semicarbazide;
1-[4-(exo-2-norbornoxy)benzyl]semicarbazide;
1-[4-(exo-2-norbornoxy)benzyl]-2-methylsemicarbazide;
1-[3-chloro-4-(4-fluorophenoxy)benzyl]semicarbazide;
1-[3-chloro-4-(4-fluorophenoxy)benzyl]-2-methylsemicarbazide;
1-[4-(phenoxy)benzyl]semicarbazide;
1-[4-(phenoxy)benzyl]-2'-methylsemicarbazide;
1-[3-[4-(2-butyl)phenoxy]benzyl]semicarbazide;

The following semicarbazides can be prepared from the corresponding semicarbazones using a similar procedure:

1-[4-(cyclohexyloxy)benzyl]semicarbazide;
1-[3-(4-methylphenoxy)benzyl]semicarbazide;
1-[4-(3,4-difluorophenoxy)benzyl]semicarbazide;
1-[4-(2,4-difluorophenoxy)benzyl]semicarbazide;
1-[4-(2,4-difluorophenoxy)benzyl]-2-methylsemicarbazide;
1-[4-(2-fluorobenzyloxy)benzyl]semicarbazide.

EXAMPLE 3

1-[4-(4-Fluorophenoxy)benzyl]semicarbazide as Anticonvulsant

The ability of 1-[4-(4-fluorophenoxy)benzyl] semicarbazide to block maximal electroshock-induced seizures (MES) was determined by the following procedure.

Seizures were induced by application of current (50 mA, 60 pulses/sec, 0.8 msec pulse width, 1 sec duration, D.C.) using a Ugo Basile ECT device (model 7801). Mice were restrained by gripping the loose skin on their dorsal surface and saline-coated corneal electrodes were held lightly against the two cornea. Current was applied and mice were observed for a period of up to 30 sec for the occurrence of a tonic hindlimb extensor response. A tonic seizure was defined as a hindlimb extension in excess of 90 degrees from plane of the body.

1-[4-(4-Fluorophenoxy)benzyl]semicarbazide was administered iv to mice 10 min before the test procedure. The compound exhibited protection against MES with an $ED_{50}$ (the dose protecting 50% of animals) of 4.2 mg/kg. 1-[3-Fluoro-4-(4-fluorophenoxy)benzyl]semicarbazide was tested po in mice and was found to have an $ED_{50}$ of 3.2 mg/kg.

EXAMPLE 4

Activity of 1-(4-(4-Fluorophenoxy)benzyl] semicarbazide as Sodium Channel Blocker 1-[4-(4-Fluorophenoxy)benzyl]semicarbazide was tested in the electro-physiological and binding assays described above and produced dose-dependent inhibition of voltage-gated sodium currents recorded HEK-293 cells stably expressing hSkM 1 sodium channels. The blocking effect of this compound on $Na^+$ currents was highly sensitive to the holding voltage, indicating that 1-[4-(4-fluorophenoxy) benzyl]semicarbazide binds to voltage-sensitive $Na^+$ channels in their inactivated states and has weak potency towards $Na^+$ channels in their resting states (Ragsdale et al., *Mol. Pharmacol.* 40:756–765 (1991); Kuo and Bean, *Mol. Pharmacol.* 46:716–725 (1994)). The apparent antagonist dissociation constant ($K_d$) of this compound for inactivated sodium channels is ~7.5 $\mu$M.

Having now fully described this invention, it will be understood by those of ordinary skill in the art that the same can be performed within a wide and equivalent range of conditions, formulations and other parameters without affecting the scope of the invention or any embodiment thereof. All patents. patent applications and publications cited herein are fully incorporated by reference herein in their entirety.

1-(4-phenoxybenzyl)semicarbazide;
1-(4-(4-fluorophenoxy)benzyl)semicarbazide;
1-(4-(4-chlorophenoxy)benzyl)semicarbazide;
1-(4-(4-bromophenoxy)benzyl)semicarbazide;
1-(4-(4-methoxyphenoxy)benzyl)semicarbazide;
1-(4-(4-trifluoromethylphenoxy)benzyl)semicarbazide;
1-(4-(4-methylphenoxy)benzyl)semicarbazide;
1-(4-(3,4-difluorophenoxy)benzyl)semicarbazide;
1-(4-(4-chloro-2-fluorophenoxy)benzyl)semicarbazide;
1-(4-(4-nitrophenoxy)benzyl)semicarbazide;
1-(4-(3-methylphenoxy)benzyl)semicarbazide;

1-(4-(4-t-butylphenoxy)benzyl)semicarbazide;
1-(4-(4-propylphenoxy)benzyl)semicarbazide;
1-(4-(4-s-butylphenoxy)benzyl)semicarbazide;
1-(4-(3,4-methylenedioxyphenoxy)benzyl)semicarbazide;
1-(4-cyclohexyloxybenzyl)semicarbazide;
1-(4-cycloheptyloxybenzyl)semicarbazide;
1-[4-(5-indanyloxy)benzyl]semicarbazide;
1-(4-(6-quinolinyloxy)benzyl)semicarbazide;
1-(4-(4-fluorophenoxy)-3-fluorobenzyl)semicarbazide;
1-(4-(tetrahydropyranyloxy)benzyl)semicarbazide;
1-(4-(4-fluorophenoxy)benzyl-4-methylsemicarbazide;
1-(4-(4-fluorophenoxy)benzyl)-2-methylsemicarbazide;
1-[(4-trifluoromethyl)benzyl]-2'-methylsemicarbazide;
1-(3-(4-methylphenoxy)benzyl)semicarbazide;
1-[(4-cyclohexylmethoxy)benzyl]semicarbazide;
1-[3-fluoro-4-(4-fluorophenoxy)benzyl]semicarbazide;
1-[3-fluoro-4-(4-fluorophenoxy)benzyl]-2'-methylsemicarbazide;
1-[4-(5,6,7,8-tetrahydro-2-naphthoxy)benzyl]semicarbazide;
1-[3-fluoro-4-(4-fluorophenoxy)-1-phenylethyl]semicarbazide;
1-[4-(3,4-difluorophenoxy)benzyl]-2-methylsemicarbazide;
1-[4-(3,5-difluorophenoxy)benzyl]semicarbazide;

What is claimed is:

1. A compound having the Formula I:

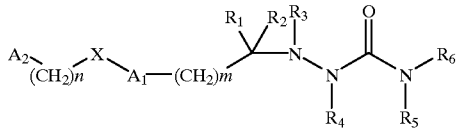

I or a pharmaceutically acceptable salt or prodrug thereof, wherein:

$R_1$ and $R_2$ are independently hydrogen, alkyl, cycloalkyl, alkenyl, alkynyl, haloalkyl, aryl, aminoalkyl, hydroxyalkyl, alkoxyalkyl or carboxyalkyl;

$R_3$, $R_4$, $R_5$ and $R_6$ are independently hydrogen, alkyl, cycloalkyl, alkenyl, alkynyl, haloalkyl, aryl, aminoalkyl, hydroxyalkyl, alkoxyalkyl or carboxyalkyl, or $R_3$ and $R_4$ are defined as above, and $R_5$ and $R_6$ together with the nitrogen atom to which they are attached form a heterocycle $A_1$ and $A_2$ are independently aryl, heteroaryl, saturated or partially unsaturated cycloalky or saturated or partially unsaturated heterocycle, any of which is optionally substituted;

X is one of O, S, $NR_7$, $CH_2$, $C(O)$, $NR_7C(O)$, $C(O)NR_7$, SO, $SO_2$ or a covalent bond; where $R_7$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3; and m is 0, 1, 2, or 3.

2. A compound according to claim 1, wherein $A_1$ and $A_2$ is phenyl optionally substituted with hydrogen, alkyl, haloalkyl, or halogen; and X is O.

3. A compound according to claim 1, wherein $A_1$ is phenyl optionally substituted with hydrogen, alkyl, haloalkyl, or halogen; and $A_2$ is 3,4-methylenedioxyphenyl, 3,4-ethyelendioxyphenyl, indanyl or naphthyl, optionally substituted with hydrogen, alkyl, haloalkyl, or halogen.

4. A compound of claim 1, having Formula II:

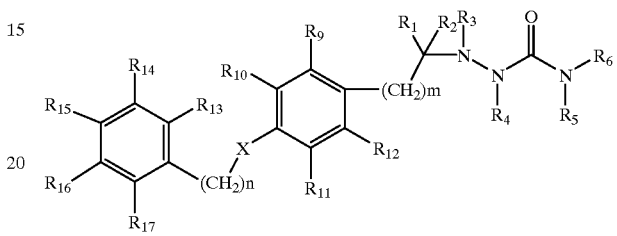

II or a pharmaceutically acceptable salt or prodrug thereof, wherein:

$R_1$, $R_2$, $R_3$, $R_4$, $R_5$, $R_6$, X, n and m are as defined previously in claim 1 with respect to Formula I; and $R_9$, $R_{10}$, $R_{11}$ and $R_{12}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamido, hydroxy, thiol, acyloxy, azido, alkoxy, carboxy, carbonylamino or alkylthiol; or $R_9$ and $R_{10}$ or $R_{11}$ and $R_{12}$ are taken together with the carbon atoms to which they are attached to form a carbocycle or heterocycle.

$R_{13}$, $R_{14}$, $R_{15}$, $R_{16}$ and $R_{17}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, hydroxy, thiol, acyloxy, azido, alkoxy, carboxy, carbonylamino or alkylthiol; or one of $R_{13}$ and $R_{14}$, or $R_{14}$ and $R_{15}$, or $R_{15}$ and $R_{16}$, or $R_{16}$ and $R_{17}$, are taken together with the carbon atoms to which they are attached to form a carbocycle or heterocycle.

5. A compound of claim 1, having Formula III or Formula IV:

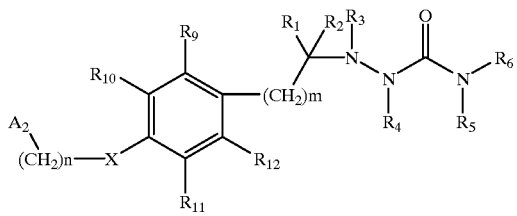

III

IV

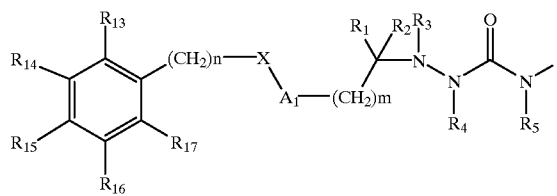

or a pharmaceutically acceptable salt or prodrug thereof, wherein:

$R_1$–$R_6$, n, m, $A_1$, $A_2$ and X are as defined previously in claim 1;

$R_9$, $R_{10}$, $R_{11}$ and $R_{12}$ independently are hydrogen, halo, haloalkyl, aryl, cycloalkyl, saturated or partially unsaturated heterocycle, heterocycle, heteroaryl, alkenyl, alkynyl, arylalkyl, arylalkenyl, arylalkynyl, heteroarylalkyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, hydroxy, thiol, acyloxy, carboxy, carbonylamino or alkylthiol; or $R_9$ and $R_{10}$ or $R_{11}$ and $R_{12}$ are taken together with the carbon atoms to which they are attached to form a carbocycle or heterocycle;

$R_{13}$, $R_{14}$, $R_{15}$, $R_{16}$ and $R_{17}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro amino, ureido, cyano, acylamino, hydroxy, thiol, acyloxy, azido, alkoxy, carboxy, carbonylamino or alkylthiol; or one of $R_{13}$ and $R_{14}$, or $R_{14}$ and $R_{15}$, or $R_{15}$ and $R_{16}$, or $R_{16}$ and $R_{17}$ are taken together with the carbon atoms to which they are attached to form a carbocycle or heterocycle.

6. A compound of claim 5, wherein $A_2$ is an optionally substituted heteroaryl or aryl group selected from the group consisting of pyridyl, pyrimidinyl, 1,3,5-triazinyl, naphthyl, quinolyl, furanyl, and thiophenyl.

7. A compound of claim 5, wherein:

$A_1$ is an optionally substituted heteroaryl or aryl group selected from the group consisting of pyridyl, pyrimidinyl, 1,3,5-triazinyl, naphthyl, quinolyl, furanyl, and thiophenyl.

8. A compound of claim 1, having the Formula V or Formula VI:

V

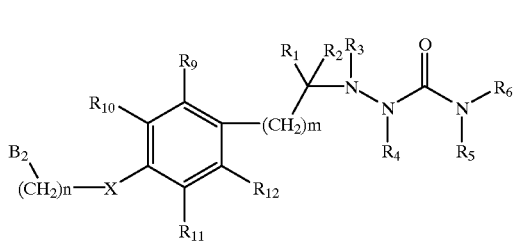

VI

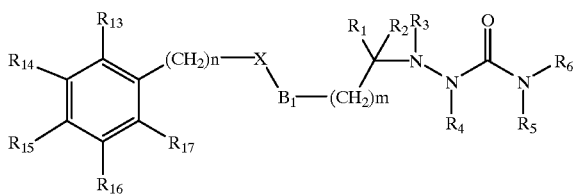

or a pharmaceutically acceptable salt or prodrug thereof, wherein:

$R_1$–$R_6$, $R_9$–$R_{12}$, $R_{13}$–$R_{17}$, n, m and X are as defined previously with respect to Formulae I and II; and $B_1$ is an optionally substituted, saturated or partially unsaturated cycloalkyl or optionally substituted, saturated or partially unsaturated heterocycle; and $B_2$ is an optionally substituted, saturated or partially unsaturated cycloalkyl or optionally substituted, saturated or partially unsaturated heterocycle.

9. A compound according to claim 8, wherein $B_1$ is cyclopentyl, cyclohexyl, cycloheptyl, tetrahydrofuranyl, tetrahydropyranyl, pyrrolidinyl or piperidinyl.

10. A compound according to claim 8, wherein $B_2$ is cyclopentyl, cyclohexyl, cycloheptyl, tetrahydrofuranyl, tetrahydropyranyl, pyrrolidinyl or piperidinyl.

11. A compound according to claim 1, wherein said compound is

1-[4-(benzyl)benzyl]semicarbazide;

1-[4-(3,4-methylenedioxyphenoxy)benzyl]-2-methylsemicarbazide;

1-[4-(5,6,7,8-tetrahydro-2-naphthoxy)benzyl]-2-methylsemicarbazide;

1-[3-fluoro-4-(5-Indanoxy)benzyl]semicarbazide;

1-[4-(exo-2-norbornoxy)benzyl]semicarbazide;

1-[4-(exo-2-norbornoxy)benzyl]-2-methylsemicarbazide;

1-[3-chloro-4-(4-fluorophenoxy)benzyl]semicarbazide;

1-[3-chloro-4-(4-fluorophenoxy)benzyl]-2-methylsemicarbazide;

1-[4-(phenoxy)benzyl]-2-methylsemicarbazide and

1-[3-[4-(2-butyl)phenoxy]benzyl]semicarbazide.

12. A pharmaceutical composition, comprising a compound of any one of claims 1–11, and a pharmaceutically acceptable carrier or diluent.

13. A method of treating a disorder responsive to the blockade of sodium channels in a mammal suffering therefrom, comprising administering to a mammal in need of such treatment an effective amount of a compound having the Formula I:

I

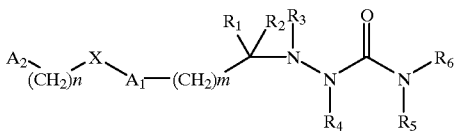

or a pharmaceutically acceptable salt or prodrug thereof, wherein:

$R_1$ and $R_2$ are independently hydrogen, alkyl, cycloalkyl, alkenyl, alkynyl, haloalkyl, aryl, aminoalkyl, hydroxyalkyl, alkoxyalkyl or carboxyalkyl;

R$_3$, R$_4$, R$_5$ and R$_6$ are independently hydrogen, alkyl, cycloalkyl, alkenyl, alkynyl, haloalkyl, aryl, aminoalkyl, hydroxyalkyl, alkoxyalkyl or carboxyalkyl, or R$_3$ and R$_4$ is defined as above, and R$_5$ and R$_6$ together with the nitrogen atom to which they are attached form a heterocycle;

A$_1$ and A$_2$ are independently aryl, heteroaryl, saturated or partially unsaturated cycloalkyl or saturated or partially unsaturated heterocycle, any of which is optionally substituted;

X is one of O, S, NR$_7$, CH$_2$, C(O), NR$_7$C(O), C(O)NR$_7$, SO, SO$_2$ or a covalent bond; where R$_7$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3; and m is 0, 1, 2, or 3.

14. The method according to claim 13, wherein A$_1$ and A$_2$ are both optionally substituted aryl moieties.

15. The method according to claim 13, wherein
A$_1$ and A$_2$ are phenyl moieties which is optionally substituted by one or two substituents independently selected from the group consisting of hydrogen, C$_{1-6}$ alkyl, halogen, hydroxy, C$_{1-4}$ alkoxy or trifluoromethyl;
R$_1$ and R$_2$ is hydrogen;
R$_3$ and R$_4$ is hydrogen or methyl;
R$_5$ and R$_6$ independently is hydrogen, C$_{1-6}$ alkyl, or C$_{3-7}$ cycloalkyl; and
X is O, CH$_2$, or NH.

16. The method according to claim 13, wherein said compound is selected from the group consisting of:
1-(4-phenoxybenzyl)semicarbazide;
1-(4-(4-fluorophenoxy)benzyl)semicarbazide;
1-(4-(4-chlorophenoxy)benzyl)semicarbazide;
1-(4-(4-bromophenoxy)benzyl)semicarbazide;
1-(4-(4-methoxyphenoxy)benzyl)semicarbazide;
1-(4-(4-trifluoromethylphenoxy)benzyl)semicarbazide;
1-(4-(4-methylphenoxy)benzyl)semicarbazide;
1-(4-(3,4-difluorophenoxy)benzyl)semicarbazide;
1-(4-(4-chloro-2-fluorophenoxy)benzyl)semicarbazide;
1-(4-(4-nitrophenoxy)benzyl)semicarbazide;
1-(4-(3-methylphenoxy)benzyl)semicarbazide;
1-(4-(4-t-butylphenoxy)benzyl)semicarbazide;
1-(4-(4-propylphenoxy)benzyl)semicarbazide;
1-(4-(4-s-butylphenoxy)benzyl)semicarbazide;
1-(4-(3,4-methylenedioxyphenoxy)benzyl) semicarbazide;
1-(4-cyclohexyloxybenzyl)semicarbazide;
1-(4-cycloheptyloxybenzyl)semicarbazide;
1-(4-(5-indanyloxy)benzyl)semicarbazide;
1-(4-(6-quinolinyloxy)benzyl)semicarbazide;
1-(4-(4-fluorophenoxy)-3-fluorobenzyl)semicarbazide;
1-(4-(tetrahydropyranyloxy)benzyl)semicarbazide;
1-(4-(4-fluorophenoxy)benzyl-4-methylsemicarbazide;
1-(4-(4-fluorophenoxy)benzyl)-2-methylsemicarbazide;
1-(3-fluoro-4-(4-fluorophenoxy)benzyl)semicarbazide;
1-(3-(4-methylphenoxy)benzyl)semicarbazide;
1-(4-trifluoromethyl)benzyl)-2'-methylsemicarbazide;
1-[3-fluoro-4-(4-fluorophenoxy)benzyl]-2-methylsemicarbazide;
1-[4-(5,6,7,8-tetrahydro-2-naphthoxy)benzyl] semicarbazide;
1-[3-fluoro-4-(4-Fluorophenoxy)-1-phenylethyl] semicarbazide;
1-[4-(3,4-difluorophenoxy)benzyl]-2-methylsemicarbazide;
1-[4-(3,5-difluorophenoxy)benzyl]semicarbazide;
1-[4-(benzyl)benzyl]semicarbazide;
1-[4-(3,4-methylenedioxyphenoxy)benzyl]-2-methylsemicarbazide;
1-[4-(5,6,7,8-Tetrahydro-2-naphthoxy)benzyl]-2-methylsemicarbazide;
1-[3-fluoro-4-(5-Indanoxy)benzyl]semicarbazide;
1-[4-(exo-2-norbornoxy)benzyl]semicarbazide;
1-[4-(exo-2-norbornoxy)benzyl]-2-methylsemicarbazide;
1-[3-chloro-4-(4-fluorophenoxy)benzyl]semicarbazide;
1-[3-chloro-4-(4-fluorophenoxy)benzyl]-2-methylsemicarbazide;
1-[4-(phenoxy)benzyl]semicarbazide;
1-[4-(phenoxy)benzyl]-2'-methylsemicarbazide and
1-[3-[4-(2-butyl)phenoxy]benzyl]semicarbazide.

17. A method for treating, preventing or ameliorating neuronal loss following global and focal ischemia; treating, preventing or ameliorating neurodegenerative conditions; treating, preventing or ameliorating pain; treating, preventing or ameliorating manic depression; providing local anesthesia; or treating arrhythmias, or treating convulsions, comprising administering to a mammal in need of such treatment an effective amount of a compound having the Formula I:

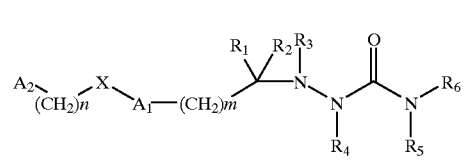

I or a pharmaceutically acceptable salt or prodrug thereof, wherein:

R$_1$ and R$_2$ are independently hydrogen, alkyl, cycloalkyl, alkenyl, alkynyl, haloalkyl, aryl, aminoalkyl, hydroxyalkyl, alkoxyalkyl or carboxyalkyl;

R$_3$, R$_4$, R$_5$ and R$_6$ are independently hydrogen, alkyl, cycloalkyl, alkenyl, alkynyl, haloalkyl, aryl, aminoalkyl, hydroxyalkyl, alkoxyalkyl or carboxyalkyl, or R$_3$ and R$_4$ is defined as above, and R$_5$ and R$_6$ together with the nitrogen atom to which they are attached form a heterocycle;

A$_1$ and A$_2$ are independently aryl, heteroaryl, saturated or partially unsaturated cycloalkyl or saturated or partially unsaturated heterocycle, any of which is optionally substituted;

X is one of O, S, NR$_7$, CH$_2$, C(O), NR$_7$C(O), C(O)NR$_7$, SO, SO$_2$ or a covalent bond; where R$_7$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3; and m is 0, 1, 2, or 3.

18. The method according to claim 17, wherein method is for treating, preventing or ameliorating pain.

19. The method according to claim 17, wherein:

$A_1$ and $A_2$ are phenyl moieties which is optionally substituted by one or two substituents independently selected from the group consisting of hydrogen, $C_{1-6}$ alkyl, halogen, hydroxy, $C_{1-4}$ alkoxy or trifluoromethyl;

$R_1$ and $R_2$ is hydrogen;

$R_3$ and $R_4$ is hydrogen or methyl;

$R_5$ and $R_6$ independently is hydrogen, $C_{1-6}$ alkyl, or $C_{3-7}$ cycloalkyl; and X is O, $CH_2$, or NH.

20. The method of claim 17, wherein:

$A_1$ is an optionally substituted aryl group selected from the group consisting of phenyl and naphthyl, and $A_2$ is an optionally substituted heteroaryl or aryl group selected from the group consisting of pyridyl, pyrimidinyl, 1,3,5-triazinyl, furanyl, thiophenyl, naphthyl, quinolyl, 3,4-methylenedioxyphenyl, 3,4-ethylenedioxyphenyl, indanyl, tetrahydronaphthyl and quinoxalinyl.

21. The method of claim 17, wherein $A_1$ is an optionally substituted aryl group selected from the group consisting of phenyl or naphthyl, and $A_2$ is an optionally substituted cycloalkyl or heterocycle selected from the group consisting of cyclopentyl, cyclohexyl, cycloheptyl, piperidinyl, morpholinyl, pyrrolidinyl, tetrahydrofuranyl, tetrahydropyranyl, cyclohexenyl, adamantyl, exo-norbornyl and cyclopentenyl.

* * * * *